United States Patent [19]

Tuccillo

[11] Patent Number: 4,573,479
[45] Date of Patent: Mar. 4, 1986

[54] SYSTEMS AND METHODS FOR MONITORING THE FETAL HEART

[75] Inventor: Mark J. Tuccillo, Southington, Conn.

[73] Assignee: American Home Products Corporation, New York, N.Y.

[21] Appl. No.: 623,735

[22] Filed: Jun. 22, 1984

[51] Int. Cl.⁴ .............................................. A61B 5/04
[52] U.S. Cl. ................................................... 128/698
[58] Field of Search ........................ 128/661, 698, 715

[56] References Cited

U.S. PATENT DOCUMENTS

| | | | |
|---|---|---|---|
| 3,388,398 | 6/1968 | Kratzer et al. | 343/17.5 |
| 3,581,735 | 6/1971 | Gentner et al. | 128/715 |
| 3,910,259 | 10/1975 | Sullivan | 128/661 |
| 3,982,528 | 9/1976 | Phillipps | 128/661 |
| 3,991,365 | 11/1976 | Takeuchi | 324/78 R |
| 4,037,151 | 7/1977 | Takeuchi | 324/78 R |
| 4,143,650 | 3/1979 | Hatke | 128/2.05 Z |
| 4,211,237 | 7/1980 | Nagel | 128/698 |

Primary Examiner—William E. Kamm
Attorney, Agent, or Firm—Edward M. Blocker

[57] ABSTRACT

For determining fetal heart rate signals representing present and one or more previous fetal heart rate cycles are processed using a correlation technique. Each correlation signal produced by this technique is further processed for substantially eliminating the possibility of detecting the fetal heart rate at twice its real rate.

13 Claims, 7 Drawing Figures

SYSTEMS AND METHODS FOR MONITORING THE FETAL HEART

BACKGROUND

The present invention relates to systems and methods for monitoring fetal heart beat events, for example, for diagnosing fetal well being.

Doppler ultrasound systems monitor motions of the fetal heart by processing ultrasonic echo signals reflected from heart walls and valves to detect the Doppler shift of the echoes induced by these moving tissue surfaces.

The echo signals, however, include large Doppler shifted components produced by motions of other tissue surfaces. For example, fetal motions as well as motions of maternal tissue surfaces introduce large artefacts in the echo signals which greatly complicate the task of deriving useful information of fetal heart activity therefrom.

Various techniques have been employed for extracting information of heart activity from the echo signals. For example, directional Doppler systems segregate the echo signals into towards and away motion components for deriving simplified signals which may be peak detected to provide generally reliable indications of fetal heart activity. However, it is thus necessary to select one of the towards or away echo components for producing a heart beat event signal and the selection of a component representing noise can result in a failure to detect one or more subsequent heart beat events. U.S. Pat. No. 4,143,650 to Hatke describes a typical directional Doppler fetal heart beat monitoring system.

U.S. Pat. No. 3,982,528 to Phillipps, assigned to the assignee of the present application, describes a system for monitoring fetal heart beat events wherein fetal heart signals from a mechanical energy transducer, such as an ultrasound transducer, are correlated against a sample signal derived from such signals corresponding to one or more previous fetal heart cycles to produce a correlation signal. A peak of the correlation signal is detected and the system produces an event signal if a new peak is not subsequently detected within a fixed delay time period thereafter. This permits the system to trigger one and only one event signal for each fetal heart cycle provided that the fetal heart rate remains within certain limits, that is, between approximately 105 to 210 beats per minute.

The fetal heart rate, however, varies within a range of about 50 beats per minute to over 200 beats per minute. Consequently, when the fetal heart rate is in the range of 50–105 beats per minute, prior art techniques, such as disclosed in Phillipps, often detect the fetal heart rate at twice the real rate. More particularly, when the ventricular ejection time approaches half the fetal heart period a fetal heart signal having two heart sounds that are nearly equidistant from each other occurs. Inasmuch as these two heart sounds when processed by systems such as Phillipps result in two correlation peaks separated in time by more than the fixed delay period, double counting of the fetal heart rate occurs.

A further complication in the use of correlation techniques in fetal heart monitoring is introduced by the nature of the correlation function which is directly related in amplitude to the energy content of the input signals. Should a large artefact component be present in the input signals, for example, due to a kick by the fetus, the correlation function can jump in amplitude causing an overload and a loss of important information.

A still further complication is introduced where a temporary loss of the signal or the presence of a spurious peak in the correlation function creates a distortion in the monitored heart rate.

SUMMARY

In accordance with one aspect of the present invention, methods for producing an event signal representative of the recurrence of a fetal heart cycle are provided. The methods comprise: producing an input signal representative of fetal heart motions corresponding to at least one fetal heart cycle; producing a comparison signal derived from portions of the input signal corresponding to at least one previous fetal heart cycle; producing a correlation signal representative of a correlation function in time between the input signal and the comparison signal; determining whether a fetal heart cycle is represented by one or two peaks of the correlation signal; producing said event signal once for each peak of the correlation function when it is determined that the fetal heart cycle is represented by a single peak of the correlation signal; and producing said event signal once for every two peaks of the correlation signal when it is determined that the fetal heart cycle is represented by two peaks of the correlation signal. By determining whether each cycle is represented by one or two peaks of the correlation function, the presence of heartbeat separation is typically detected and it can be determined to produce only one event signal for the two peaks of the correlation function which in fact represent only a single heartbeat event. Accordingly, double counting resulting from these effects can be avoided. Likewise, the subsequent determination that each heartbeat event is represented by a single peak of the correlation function permits the production of an event signal for each peak of the correlation function to avoid half counting.

In accordance with a further aspect of the present invention, a system for producing an event signal representative of the recurrence of a fetal heart cycle event is provided, enjoying the same advantages of the above described method. The system comprises means for producing a data signal representative of fetal heart motions corresponding to at least one fetal heart cycle; means for storing a comparison signal derived from portions of the data signal corresponding to at least one previous fetal heart cycles; and data processing means for producing a correlation signal representative of a correlation function in time between the data signal and the comparison signal. The data processing means is operative to determine whether a fetal heart cycle is represented by one or two peaks of the correlation signal; the data processing means being further operative to produce said event signal once for each peak of the correlation function when it is determined that the fetal heart cycle is represented by a single peak of the correlation signal, and to produce said event signal once for every two peaks of the correlation signal when it is determined that the fetal heart cycle is represented by two peaks of the correlation signal.

In accordance with a still further aspect of the present invention, a system for producing an event signal representative of the recurrence of a fetal heart cycle is provided, comprising: means for producing a data signal representative of fetal heart motions corresponding to at least one fetal heart cycle; means for producing a correlation signal representative of a correlation function in time between the data signal and a comparison signal derived from portions of the data signal corresponding to at least one previous fetal heart cycle; the correlation signal producing means comprising a digital central processing means having an N bit data bus and a digital multiplier/accumulator unit, the multiplier/accumulator unit being operative to provide a sum of products of digitized values of the data signal multiplied by respective digital values of the comparison signal shifted in time relative to the data signals, said sum of products being a binary word of length N+M bits; the central processing means being operative to select an N bit sequence of bits from the sum of products as the most significant bits of the correlation signal in response to an AGC signal produced by the central processing means and varying with the energy in the data signal; the correlation signal producing means being operative to produce an event signal representative of the recurrence of a fetal heartbeat based upon the correlation signal. The system thus adjusts the amplitude of the correlation signal in accordance with the energy level of the data signal which typically varies widely in clinical monitoring thus to maintain the amplitude range within acceptable limits. The system also is permitted to operate efficiently by limiting the number of words of each correlation signal.

In accordance with yet another aspect of the present invention, a system is provided for producing an event signal representative of the recurrence of a fetal heart cycle, comprising: means for producing an input signal representative of fetal heart motions; means for producing a recurrence signal based on the input signal and representing a probable recurrence of a fetal heart cycle; and means for producing said event signal in response to the recurrence signal only if the beat to beat period represented thereby is within a range of acceptable periods predetermined by the values of one or more previous beat to beat periods. Accordingly, a temporary loss of the signal or the presence of a spurious peak in the correlation function giving rise to a temporary distortion of the monitored heart rate can often be corrected for.

In accordance with a yet still further aspect of the present invention, a system for producing an event signal representative of the recurrence of a fetal heart cycle event is provided, comprising: means for producing an analog signal representative of fetal heart motions; peak detecting means for producing a reference signal proportional to the peak detected analog signal; low pass filtering means for producing a low pass filtered analog signal from the analog signal; analog to digital converting means having a reference input coupled to receive the reference signal and an analog signal input coupled to receive the low pass filtered analog signal for converting the low pass filtered analog signal to a digital signal; and digital signal processing means for producing the event signal based upon a correlation function in time between the digital signal and a comparison signal. Since the peak detecting means receives the analog signal to produce a peak detected version thereof, the peak detecting means is enabled to adjust the amplitude of the reference signal rapidly in response to noise bursts present from time to time in the analog signal, thus to avoid overloading the analog to digital converting means due to the presence of such noise bursts in the analog signal.

BRIEF DESCRIPTION OF THE DRAWINGS

The present invention, as well as further objects and features thereof, will be understood more clearly from the following description of certain preferred embodiments, when read with reference to the accompanying drawings, in which.

DETAILED DESCRIPTION OF CERTAIN PREFERRED EMBODIMENTS

Figure 1:
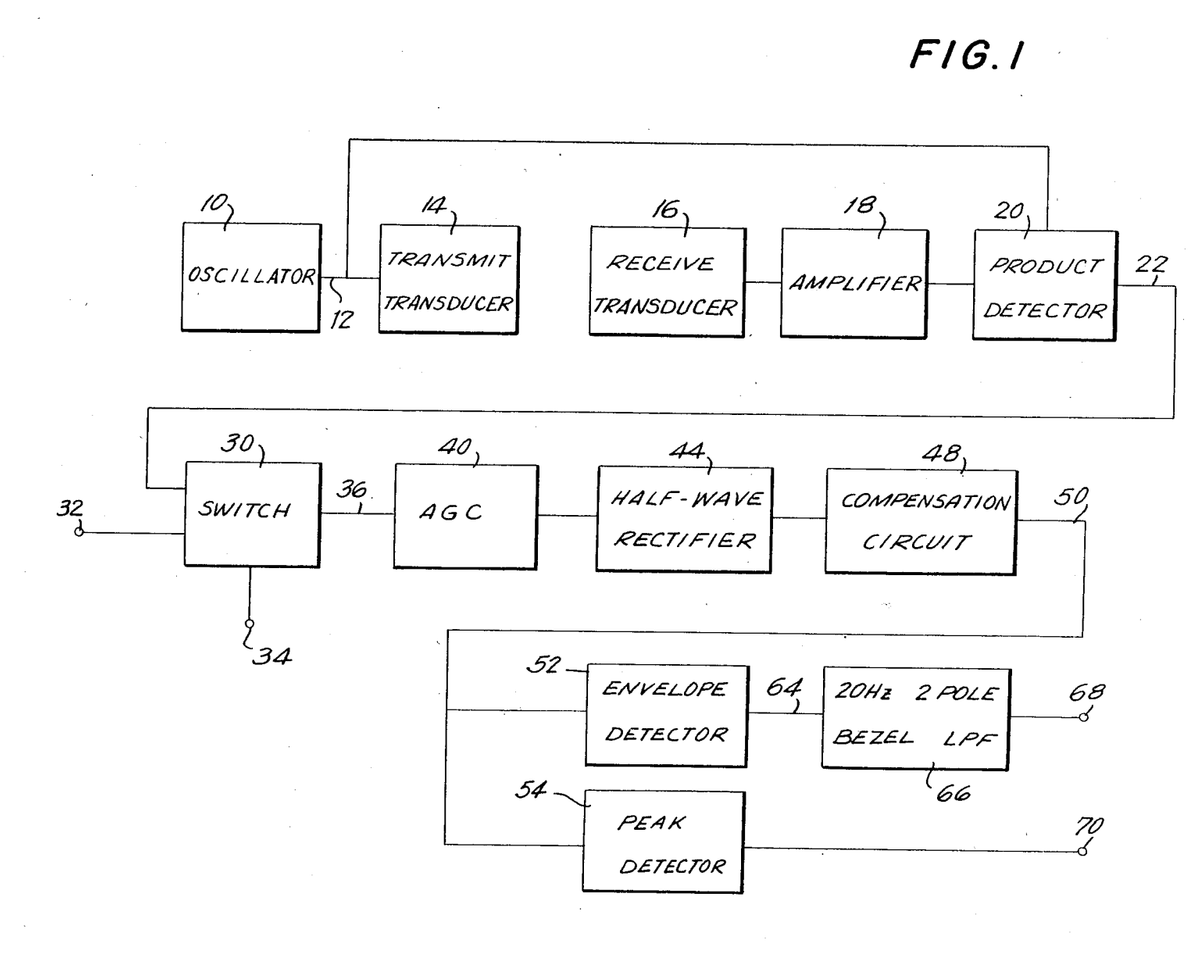
FIG. 1 is a block diagram of a front end portion of a continuous wave Doppler ultrasound fetal heart monitor, in accordance with one embodiment of the present invention.

With reference to FIG. 1, an oscillator 10 produces a continuous wave, 2.3 MHz voltage on an output terminal 12 coupled to a transmit transducer 14. Transducer 14 is a piezoelectric crystal operative to produce a 2.3 MHz, continuous acoustic wave to be coupled through a maternal abdomen to insonify the fetal heart. Acoustic echoes from within the maternal abdomen, including Doppler shifted components reflected by the walls and valves of the fetal heart, are transduced to an electrical signal by a receive transducer 16. Transducer 16 includes one or more piezoelectric crystals mounted in a common housing with transducer 14 for placement against a maternal abdomen.

The electrical signal produced by transducer 16 is amplified in amplifier 18 and supplied to one input of a product detector 20. A second input of product detector 20 is coupled with output terminal 12 of oscillator 10 to receive the continuous wave, 2.3 MHz voltage therefrom. Product detector 20 is operative to produce a base band Doppler signal having a bandwidth of at least 200 to 600 hertz at an output terminal 22. The base band Doppler signal includes components representing motions of tissue surfaces insonified by the acoustic energy produced by transducer 14. The base band Doppler signal, therefore, is likely to contain several components in addition to components representing fetal heart motions. In particular, the base band Doppler signal typically includes randomly occurring components representing fetal movements, such as a kick by the fetus, which often contain large amounts of energy. It is, therefore, desireable that the circuitry for processing the Doppler signal to extract accurate information of fetal heart activity, be protected from overloading and have the ability to distinguish signal components representing such activity from other interferring components of diverse origin. Improved circuitry for carrying out these objects is disclosed hereinbelow.

With reference again to FIG. 1, the output terminal 22 of product detector 20 is coupled to a first fixed terminal of an electronic switch 30. A second fixed terminal 32 of switch 30 is coupled to a high-Q, 80 Hz bandpass filter (not shown) having an input coupled to a phonotransducer (not shown) adapted to be placed against the maternal abdomen to provide a phono input in place of the base band Doppler signal, when desired. Switch 30 has a control terminal 34 to which a control signal may be applied for selectively coupling an output terminal 36 of switch 30 to one of its two fixed input terminals for the selection of the desired one of the Doppler signal and the phono signal for the extraction of useful information of fetal heart activity.

Output terminal 36 of switch 30 is coupled to an input of a conventional automatic gain control (AGC) circuit 40. AGC circuit 40 has a relatively slow response time to provide gain compensation for long term signal level variations. Accordingly, AGC circuit 40 will pass high energy transient components, such as those due to a fetal kick, largely unattenuated.

An output of AGC circuit 40 is coupled to an input of a half-wave rectifier 44 which serves to provide a DC version of the input signal for further signal processing. The output of rectifier 44 is coupled to an input of a compensation circuit 48, described in greater detail below. An output terminal 50 of compensation circuit 48 is coupled to an input of an envelope detector 52 and to an input of a peak detector 54.

Figure 2:
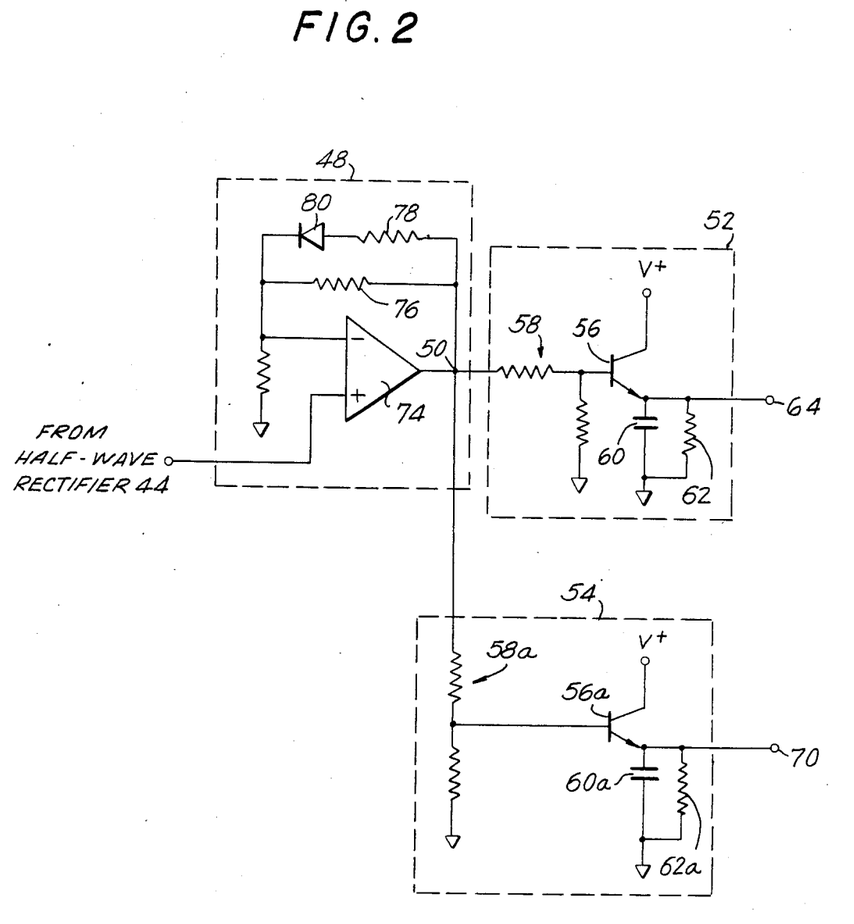
FIG. 2 is a schematic diagram of a compensation circuit, envelope detector and peak detector of the FIG. 1 embodiment.

Compensation circuit 48, envelope detector 52 and peak detector 54 are illustrated in greater detail in FIG. 2. Each of envelope detector 52 and peak detector 54 has an NPN transistor, respectively 56 and 56a, having its collector connected to a source of positive DC voltage V+ and its base coupled to the output of a resistive voltage divider, respectively 58 and 58a. The emitter of each of transistors 56 and 56a is coupled to a first terminal of a respective capacitor, 60 and 60a, whose other terminal is coupled to ground. In addition, the emitter of each of transistors 56 and 56a is coupled to a first terminal of a respective resistor, 62 and 62a, whose other terminal is coupled to ground.

With reference also to FIG. 1, envelope detector 52 has an output terminal 64 coupled to an input of a 20 Hz, 2 pole, low pass Bessel filter (LPF) 66 operative to provide a data signal at an output terminal 68 (either derived from the base band Doppler signal or the phono signal) to be converted to digital format by an analog-to-digital (A/D) converter (described hereinbelow). Peak detector 54 has an output terminal 70 coupled to the reference input of the A/D converter to provide a reference signal thereto derived from the signal input to envelope detector 52.

The voltage at output terminal 70 will rise rapidly with signal excursions exceeding the decaying voltage stored previously in capacitor 60a. The values of capacitor 60a and resistor 62a are selected to provide a decay time constant of several times the maximum expected heart beat period. For example, a decay time constant of 4.7 sec. may be selected as approximately two times a maximum expected heart beat period of 2 sec. Accordingly, as a large energy transient, for example due to a fetal kick, is received by transducer 16, the reference voltage at output 70 of peak detector 54 will closely track any signal excursions thereof above the previously stored reference voltage, thus avoiding large signal excursions at the output of the A/D converter. It will be noted that the base band Doppler signal or the phono signal has not been significantly low pass filtered before application to peak detector 54 so that the reference voltage reacts quickly to such transients to avoid producing large digital values which when multiplied together would otherwise overload the multiplier/accumulator 106 (described below). However, the relatively long decay time constant provides a stable reference to the A/D converter in the absence of such large signal excursions.

The envelopes of the fetal heart beat audio and Doppler signals exhibit exponential decay with time. Therefore, it is the purpose of envelope detector 52 to eliminate the high frequency components of the input signal while causing its output signal to closely track the naturally exponentially decaying envelope of the input signal. For example, the value of capacitor 60, together with that of resistor 62 and the input impedance of the Bessel filter 66 (which is essentially resistive) are selected to provide a decay time constant of about 75 milliseconds.

Low pass filter 66 serves to round off the peaks present in the envelope detected output of detector 52 and to limit the frequency content thereof essentially to 20 Hz. The 20 Hz break point is selected to limit the frequency content of the data signal to the A/D converter to approximately one tenth of the sampling rate, which is selected as 200 Hz.

With reference particularly to FIG. 2, compensation circuit 48 includes an operational amplifier 74 connected in a non-inverting configuration with its noninverting input coupled to the output of half-wave rectifier 44 and its output coupled to terminal 50. The negative feedback loop of amplifier 74 includes a resistor 76 having a relatively high value coupled between the output of amplifier 74 and its inverting input. In addition, the negative feedback loop includes a resistor 78 having a relatively low value coupled at one terminal to the output of amplifier 74 and at the other to the anode of a diode 80. The cathode of diode 80 is coupled to the inverting input of amplifier 74. This configuration provides an antilogarithmic response up to an output voltage sufficient to render diode 80 substantially a short circuit, which tends to compensate for the essentially logarithmic response of transistors 56 and 56a of circuits 52 and 54 at low input voltages. Once diode 80 has been forward biased sufficiently, the transfer function of compensation circuit 48 is essentially linear to correspond with the linear response of circuits 52 and 54 in this range.

Figure 3:
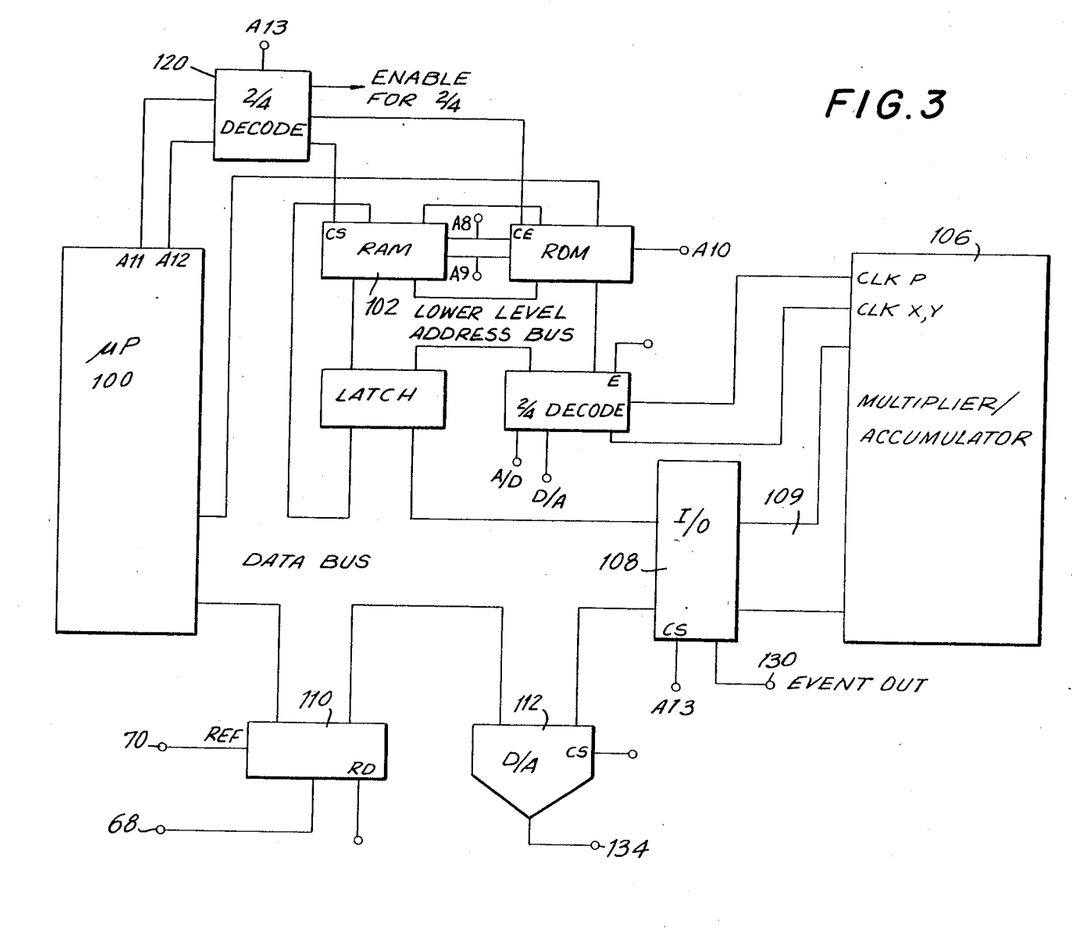
FIG. 3 is a block diagram of a digital signal processor portion of the FIG. 1 embodiment.

FIG. 3 illustrates a microprocessor based digital correlator system. The correlator system includes a microprocessor (up) 100 clocked at 10 MHz such as an Intel 8085; a 1K word RAM 102; a 2K word ROM 104; and a multiplier/accumulator 106, such as a TRW TDC 1008J. Access to RAM 102 and ROM 104 is achieved directly over the data bus of the microprocessor, whereas access to the multiplier/accumulator 106 (with the exception of its clock inputs) is through an input-/output (I/O) chip 108, interconnected thereto over an I/O bus 109, I/O 108 may be, for example, an Intel 8156-2. The system further includes an analog-to-digital converter 110 and a digital-to-analog converter 112 each coupled directly to the data bus.

I/O 108 includes 256 words of RAM which is selected by a high level on terminal address bit A 13 of microprocessor 100 coupled to the chip select (CS) input of I/O 108, while the remaining memory devices are selected when A 15 is low by decoding a combination of address bits A 11, A 12, AD 0 and AD 1. Bits A 11 and A12 are decoded by two to four decoder 120 to select one of the RAM 102 or ROM 104, or else to enable a second two to four decoder 122. Decoder 122, when selected, decodes bits AD 0 and AD 1 to generate a chip select for A/D 110 or D/A 112, or else to clock the multiplier/accumulator 106 (the X, Y multiply clock input of multiplier/accumulator 106 being tied to the third output of decoder 122, and the P accumulate clock thereof being tied to the fourth output of decoder 122). By memory mapping the clock inputs of the multiplier/accumulator 106 relatively high speed multiplication and accumulation to form a correlation function is advantageously achieved.

The sampling of data by A/D 110 is performed periodically, e.g. every five msec. under the control of an interrupt provided to microprocessor 100 from I/O 108. I/O 108 produces the interrupt pulse by dividing the clock pulse from the microprocessor 100 by an appropriate factor programmed upon system startup. As explained before, the analog to digital conversion is performed using the output of peak detector 54 supplied on terminal 70 as a reference to A/D 110, to minimize the likelihood of overloading multiplier/accumulator 106 due to sudden large artefact signals, e.g. due to a fetal kick.

The operation of the correlator system of FIG. 3 is explained with reference to the flow charts of FIGS. 4A, 4B, 4C and the waveforms of FIG. 5. Briefly, the correlator system is provided with an ultrasonic Doppler return signal or phono signal, processed as described hereinabove. The system proceeds to form a standard digital auto-correlation function thereon utilizing a stored time-delayed segment of the signal as a comparison signal and processes a digital signal representative of the correlation function to generate an event signal representative of the recurrence of a fetal heart cycle event. The event signal is output as one bit on an Event Out terminal 130 of I/O 108. The processing of the results of the correlation is carried out, in accordance with one aspect of the present invention, to more effectively detect and compensate for heartbeat separation which results in two peaks of the correlation function per heartbeat event, instead of only one peak per event. When the system detects heartbeat separation, it produces an event signal once for every two peaks of the correlation function; likewise, when the system detects that the fetal heart cycle is represented by one peak of the correlation function, (in the absence of heartbeat separation) the event signal is produced once for each peak of the correlation function. When it is desired to view the correlation function directly or to store an analog version thereof, an analog version of the digital correlation signal is acquired from output terminal 134 of D/A 112.

Figure 4A:
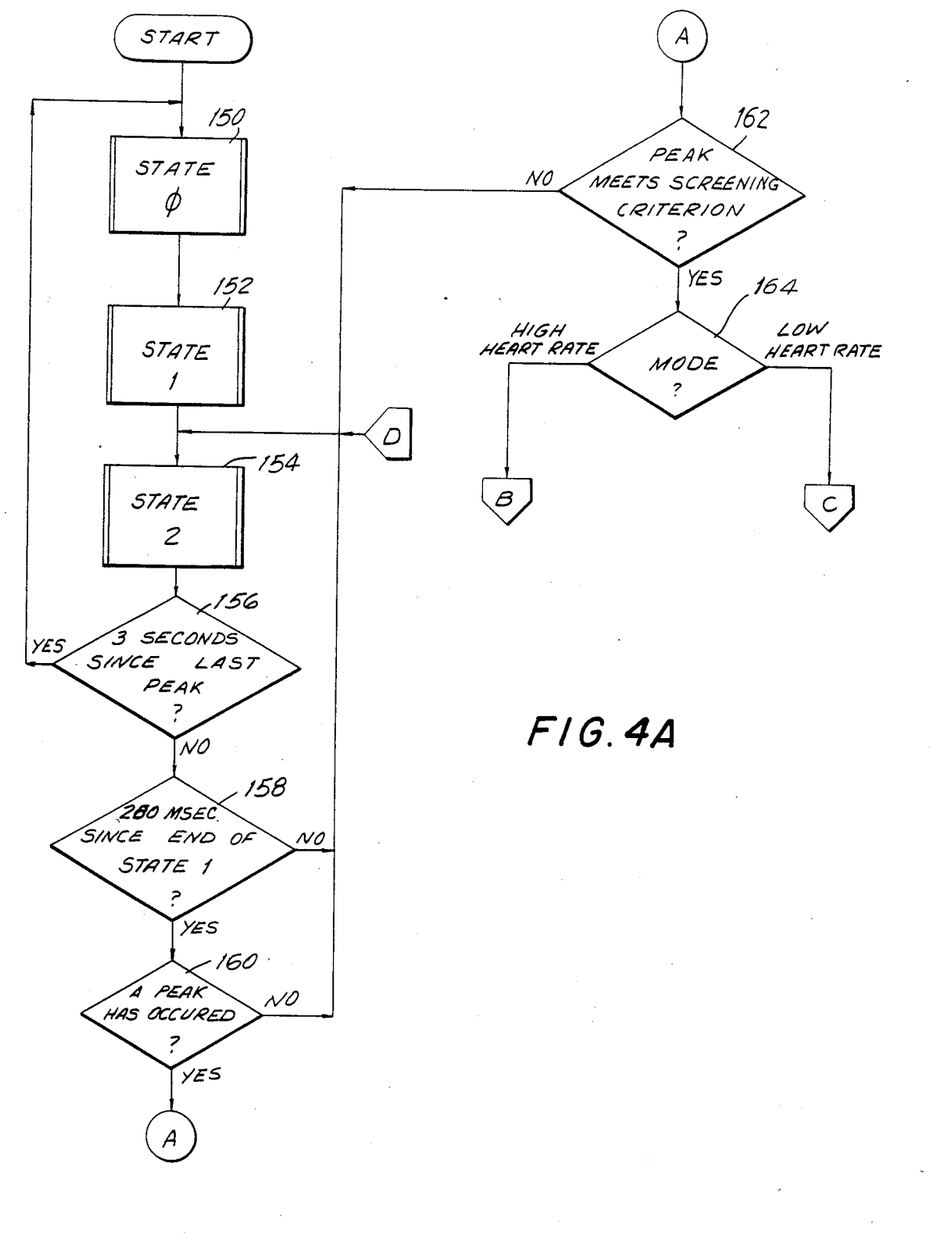
FIGS. 4A, 4B and 4C are flow chart diagrams illustrating the operation of the digital signal processor of FIG. 3.
Figure 4B:
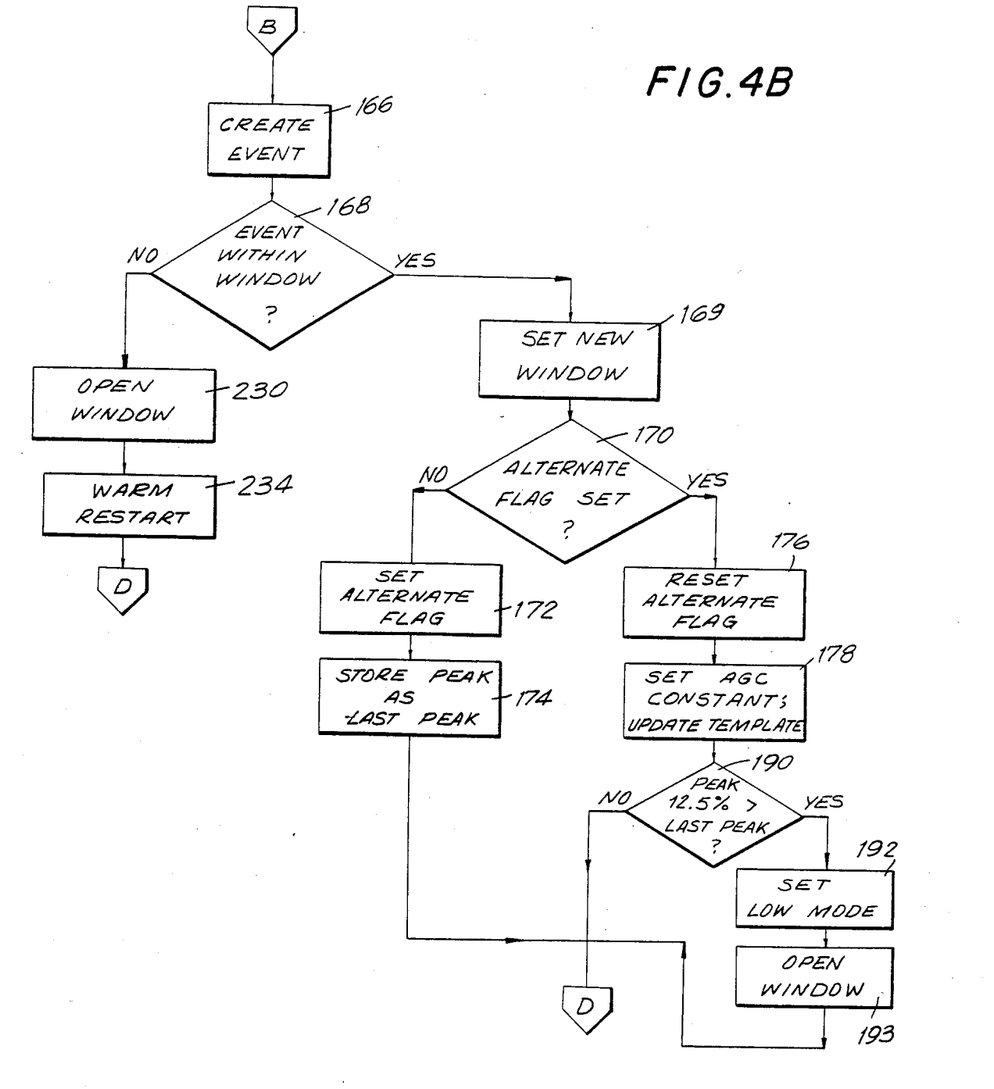
Figure 4C:
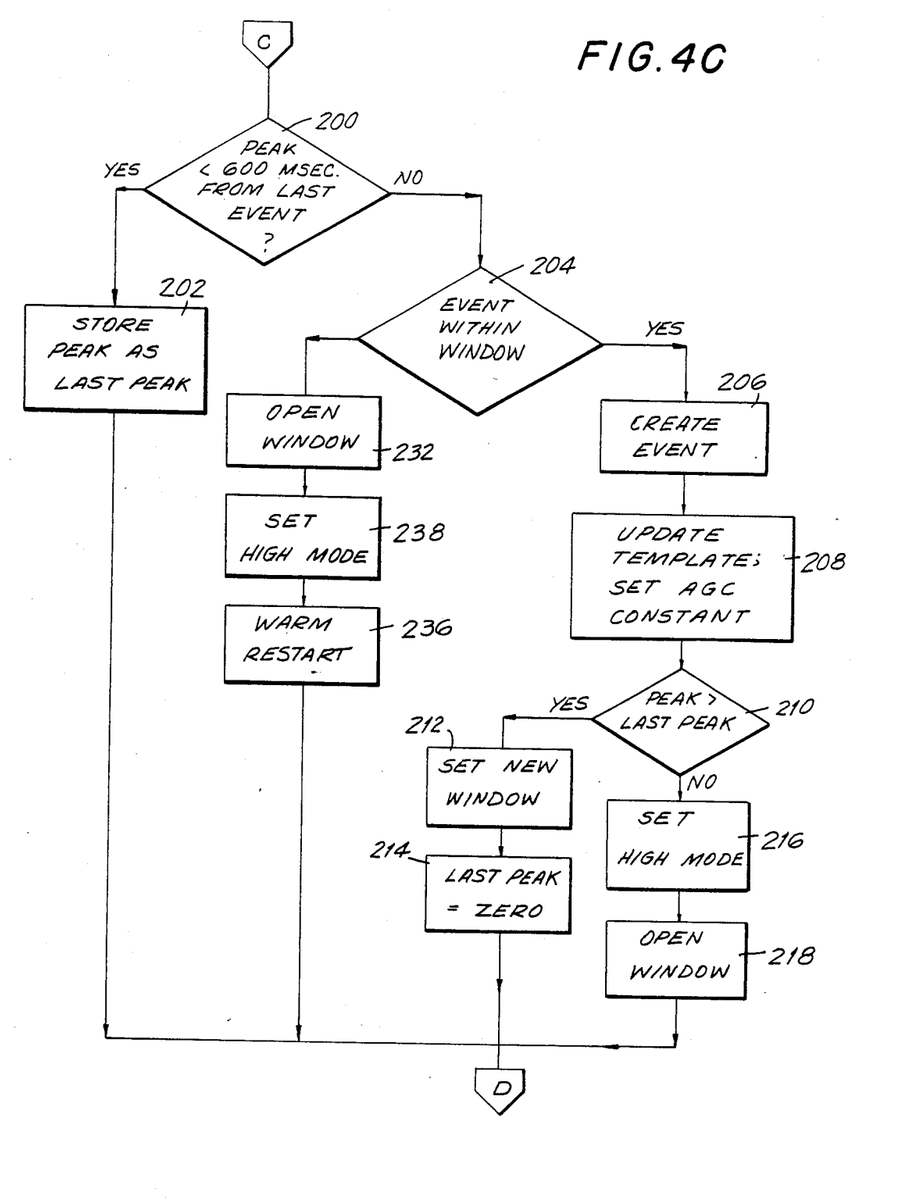
Figure 5:
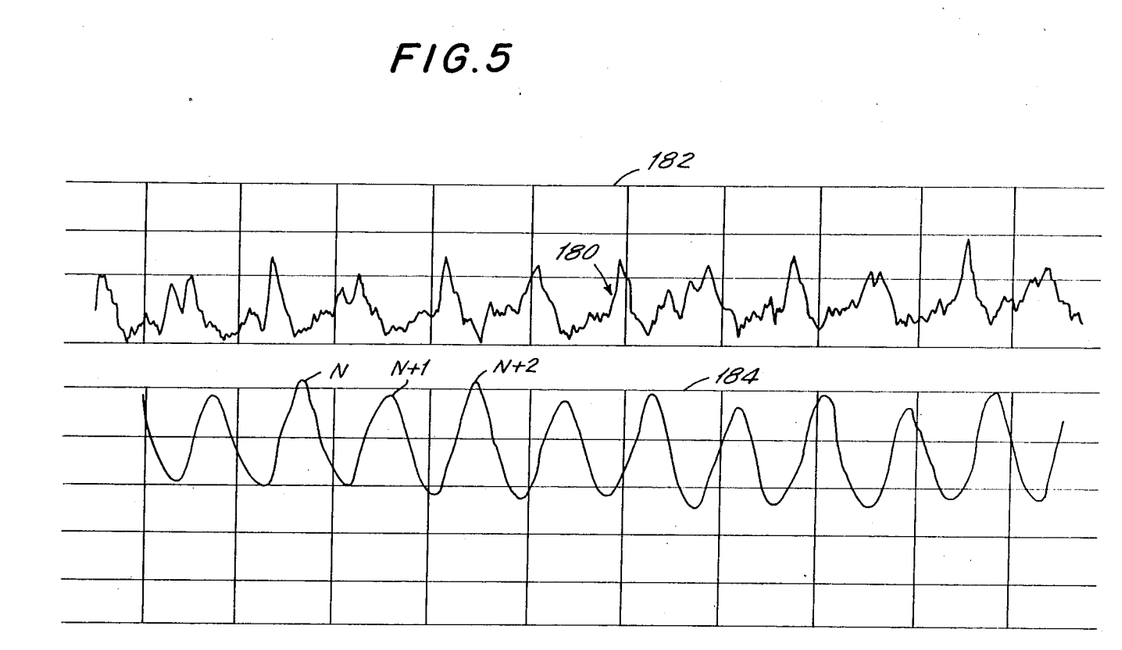
FIG. 5 is a waveform diagram illustrating one possible base band Doppler return signal obtainable with the FIG. 1 embodiment and corresponding correlation function of a digitized version thereof with a template signal selected as a prior portion of the digitized version.

Upon startup, as indicated by 150 in FIG. 4A, the system enters State ∅, wherein the flags, constants and variables are initialized, I/O 108 is set up, etc. Thereafter, State 1 (step 152) is entered, wherein the system proceeds to acquire and store an 8-bit digital version (i.e. a sample) of the signal provided at the input of A/D converter 110, to determine a correlation function based on these samples and to initially set an automatic gain control (all of which are discussed in detail below). Sampling of the signal at the input of the A/D converter 110 occurs every 5 msec. at the present embodiment until in end of State 1, an interrupt forces the system to perform another A/D conversion and to store the result of this conversion in two software registers: a data register which stores the most recent 256, 8-bit digitized samples and a template register which also stores 256, 8-bit digitized samples of the input signal (although not necessarily the most recent samples) for forming the correlation function with the contents of the data register.

It will be appreciated that after 1.28 sec. of data sampling, the data and template registers will be filled.

Thereupon, and for the reasons set forth below, the system performs a digital correlation function between the identical signals stored in the data and template registers. It will be appreciated that the result of this correlation will be proportional to the average energy content of the digitized signal for the 1.28 sec. during which the signal was sampled.

Multiplier/accumulator 106 forms the correlation function in the FIG. 3 embodiment by multiplying corresponding eight bit signals from the data and template registers and forming a sum of these multiplications in its accumulator, which in the embodiment of FIG. 3 is a nineteen bit register. In State 1, the result of the correlation of the identical signals in the data and template registers forms the basis for generating an automatic gain control (AGC) signal which directs the system to select the seven most significant, non-zero bits of this sum, together with the next higher order bit as the most significant bits of the correlation function. It will be seen that the system is thus able to adjust its operation in accordance with the strength of the incoming signals, thus to permit the correlation function to be represented by a signal of fixed word length and to form a basis for comparing sequential peaks of the correlation function for determining whether heartbeat separation is present in the incoming signal. The selection of the next higher order bit above the most significant non-zero bit as the most significant bit of the correlation function leaves a margin to accommodate noise (most likely from fetal motion) in the signal, thus to reduce the likelihood of an overload.

Upon the completion of State 1, the system proceeds to State 2, indicated by 154, wherein a new data sample is taken and stored in place of the oldest sample stored in the data register (without storing it also in the template register, now full) and a further correlation is performed. State 2 thereafter is entered only by an interrupt received from I/O 108, with one exception.

When step 154 is completed, step 156 is performed wherein the system determines whether three seconds have elapsed since the occurrence of the last peak of the correlation function. If so, the signal may have been lost, for example, due to a shift in fetal position or disconnection of a transducer. The system must, therefore, be reinitialized and the program branches to State ∅ (step 150) to do so.

If, in step 156, three seconds have not elapsed since the last peak, step 158 is performed. It is assumed in the present embodiment, that the maximum heart rate will be 210 beats per minute; accordingly, the minimum heartbeat period is 280 msec. and it is, thus, pointless to test for the occurrence of a peak in the correlation function until 280 msec. have expired from the end of State 1. Until the expiration of this time period, therefore, the system waits at this point until a new interrupt occurs, whereupon State 2 is once again entered.

Once it is determined that 280 msec. have expired from the end of State 1, the program proceeds from step 158 to step 160, wherein the correlation function is tested to determine whether a peak thereof has occurred. If not, the program waits for an interrupt, and thereupon returns to State 2 once again. If a peak has occurred, the program proceeds to step 162 for initially screening the peak to determine whether it is only a local peak or whether it is likely to represent the recurrence of a heartbeat event.

The screening function of step 162 accepts a peak of the correlation function as a possibly valid peak only after a peak free delay of predetermined length, which in the present disclosed embodiment is 280 msec. The screening function of step 162, therefore, is to return the program to State 2, unless 280 msec. has transpired since the peak was detected without the occurrence of a new peak (hereinafter "screening criterion").

In order to provide data for generating an AGC constant (as described hereinabove) based upon the signals which produced the most recent peak of the correlation function, every time a peak is detected in step 160, a third register begins to store the oldest data from the data register which otherwise would have been written over by new data entering the data register. After a determination in step 162 that screening criterion is met, and upon a subsequent determination that an event signal should be produced as made in the manner described hereinbelow, the old data in the third register is exchanged with the newest 280 msec. of data from the peak now stored in the data register. Then the contents of the data register are substituted for that in the template register and a correlation is performed to produce the AGC signal. The template register is thereby updated for use in performing correlations with new data entered in the data register. Thereafter, the new data stored temporarily in the third register is substituted for the oldest data in the data register. In this way, while the new AGC signal is being produced, none of the newest samples are lost.

Once it is determined that a given peak of the correlation function satisfies the screening criterion, the program proceeds to analyze the most recent peak against the next most recent peak of the correlation function for determining whether to produce an event signal for each peak satisfying the screening criterion or an event signal for every other such peak of the correlation function (two peaks occurring for each heartbeat event due to separation of heart sounds). The foregoing analysis is based on a dual operational mode, wherein a previous determination that the heartbeat event was represented by one or two peaks predetermines the mode of operation in analyzing subsequent peaks. That is, if from an analysis of a previous peak pair, it was determined that the event corresponded with only one peak, a "high heart rate" mode of operation is predetermined for subsequent analysis; whereas, a "low heart rate" mode is predetermined for subsequent analysis if it was previously determined that two peaks represent each event.

The subsequent mode is predetermined by a two-state "mode" flag tested in step 164, whereupon the appropriate branch to the high heart rate mode (illustrated by FIG. 4B) or the low heart rate mode (illustrated in FIG. 4C) is executed. In State 0 (step 150), the mode flag is initialized in the high heart rate mode. Accordingly, when the first peak satisfying the screening criterion is detected, the program proceeds through step 164 to step 166 (FIG. 4B) and an event signal is produced (since each such peak in the high heart rate mode represents the recurrence of a heartbeat event).

After the performance of succeeding step 168 to determine whether the event falls within a window of acceptability (as described hereinbelow), and a new window is set in step 169 (assuming the event fell within the window), an "alternate" flag is tested in step 170. The alternate flag (reset in State 0), which toggles each time the routine of FIG. 4B is performed assuming the event fell within the window, causes two successive peaks of the correlation function to be tested so that it can be determined whether their relative amplitudes indicate that heartbeat separation is present, so that the mode flag will be toggled and, with detection of the next peak satisfying the screening criterion, the low heart rate mode will be entered. As noted above, the alternate flag is initially reset in State 0, and so from step 170, the program proceeds through step 172, wherein the Alternate Flag is set, to step 174, in which the correlation signal representative of the peak is stored as "Last Peak". It is noted that the template register is not updated at this time.

Upon receipt of a further peak satisfying the screening criterion, the program proceeds through steps 164-169 (assuming the event is within the window) to step 170, wherein it is determined to branch to step 176, since the alternate flag was set previously in step 172. From step 176 (in which the alternate flag is reset, i.e., again toggled), the program proceeds to step 178 wherein the operations of setting the AGC signal and updating the template, as described above, are performed.

It will be seen that, since the template is updated only once for every two peaks of the correlation function, the same template was used in producing both peaks. The amplitude of the correlation function between time shifted signals provides a measure of the sameness of the signals; i.e., signals which are like one another produce a correlation function having a relatively high amplitude compared to that produced between dissimilar signals (provided the same comparison signal is used in each case). If each peak represents a single heartbeat event, then Last Peak should have about the same or greater amplitude then the more recent (i.e. newest) peak.

If, however, heartbeat separation is encountered, then successive peaks of the correlation signal represent different segments of a single heartbeat event. FIG. 5 illustrates at 180 an exemplary Doppler return signal representative of fetal heart motions wherein heartbeat separation is present, plotted with time on a grid 182 such as that appearing on strip chart paper. Next to grid 182 is a second grid 184 illustrating an exemplary correlation signal 186 representative of a correlation function between segments of the signal 180 against a prior segment thereof which is at least one heartbeat event in length and is updated after every two peaks of signal 186.

If it is assumed that a template update took place upon the detection of peak N of signal 186, then peak N+1, representative of a different heart motion, will have a relatively low amplitude since different heart motions give rise to signals having distinctively different patterns and the correlation resulting in peak N+1 was performed between signals representing different heart motions. However, peak N+2 has a greater amplitude than that of peak N+1, since it represents the correlation of signals representing the same heart motions.

After the performance of step 178 (FIG. 4B) a correlation peak Last Peak and a more recent peak, both obtained by correlations against the same template, are compared in step 190. If the more recent peak is at least 12.5% greater than Last Peak (in the preferred embodiment of the present invention), it is determined that heartbeat separation is occurring, and the low heartbeat mode is set (step 192) and, upon detection of the next peak satisfying the screening criterion, the low heartbeat mode routine (FIG. 4C) will be performed (note also that the window is opened per step 193, as will be explained below). If, conversely, the more recent (i.e. new) peak fails to exceed Last Peak by at least 12.5%, the system remains in the high heartbeat mode. By requiring that the new peak exceed Last Peak by a substantial margin, random variations in amplitude between successive peaks representative of separate heartbeat events are not likely to trigger a change to a low heartbeat mode, which would result in half counting.

If, however, a change in mode occurs, the program will proceed from step 164 (FIG. 4A) to step 200 (FIG. 4C) upon the detection of the next peak satisfying the screening criterion. In step 200, it is determined whether the most recent peak occurred less than a predetermined time period from the last heartbeat event (the predetermined time period in the preferred embodiment is 600 msec.). If so, this peak is stored (step 202) as Last Peak and the program returns to State 2 (FIG. 4A) upon the next interrupt. If not, it is determined (step 204) whether an event as indicated by the peak would fall within the window of acceptability (discussed in greater detail below).

Assuming for now that step 204 yields a positive result, an event signal is produced (step 206), the AGC signal and the template register are updated (step 208). Succeeding step 210 in the preferred embodiment determines whether the most recent peak exceeds Last Peak in amplitude, in which case it is decided that the program should remain in the low heart rate mode. If heartbeat separation is present, then the second peak following an event and a template update should have a greater amplitude than the immediately preceeding peak stored as Last Peak. Accordingly, this condition is tested in step 210 and an affirmative result leaves the program in the low heart rate mode, while a new window is set in step 212 (as explained below) and Last Peak is reset to zero in setp 214.

One of the purposes of State 0 (step 150) is to initialize Last Peak as zero. Accordingly, Last Peak is zero until the low heart rate mode is entered and a peak occurs within 600 msec. of the last event. Thereafter, as long as the program remains in the low heart rate mode, Last Peak will be reset to zero in step 214. Accordingly, the absence of heartbeat separation at heart rates below 100 beats per minute resulting in a single peak per event (while in the low heart rate mode) ensures that each peak will be counted as an event, since step 200 will yield a negative result and step 210 will yield a positive result, so that Last Peak remains equal to zero (step 214).

If, however, the heart rate increases above 100 beats per minute while the program is still in the low heart rate mode, then a peak representing an event will occur less than 600 msec. from the last event. This peak will be stored as Last Peak (steps 200 and 202) and will be compared against the new (i.e. next) peak in step 210. Since Last Peak and the new peak were produced with the use of the same template, it is improbable that Last Peak will be less than the new peak in amplitude (since the signal giving rise to Last Peak is more likely to resemble the data in the template register than is the signal giving rise to the new peak, which is more remote in time from the signal stored in the template register).

If step 210 yields a negative result, step 216 changes the mode to the high heart rate mode and the window is opened in step 218 (as explained below). Accordingly, upon the occurrence of the next peak satisfying the screening criterion, the program will enter the high heart rate mode from step 164.

Occasionally the Doppler or phono signal becomes contaminated by noise, which could originate from one or more diverse sources, such as fetal movement. Such noise can give rise to spurious peaks in the correlation function. In order to reduce the likelihood that noise will lead to a false event signal, each time an event signal is to be output, the system determines whether the event will fall within a predetermined "window" (i.e., a range of acceptable heart beat periods predetermined by the values of one or more previous beat to beat periods). It will be appreciated that the window may be defined equivalently in terms of the heart rate represented by one or more previous beat to beat periods. In the present embodiment, the window is predetermined as a range of heartbeat periods corresponding to a range of heart rates which includes those within twenty beats per minute greater or less than the heart rate represented by the last beat to beat period.

In the present embodiment, therefore, after each event is accepted as within the predetermined window, a new window is set in the manner described above, with one exception. See step 169 of FIG. 4B and step 212 of FIG. 4C. Where it is decided that a mode change is necessary, however, the previously set window is no longer useful; according, the window thereupon is "opened", i.e. it is then set as the entire range of possible heart rates, in the present embodiment from zero to 240 beats per minute. See step 193 of FIG. 4B and step 218 of FIG. 4C. Since it is not known beforehand what the present beat to beat heart rate is, a further initialization performed in State 0 is to open the window in the manner described above.

As noted above, every time it is found that a peak satisfies the screening criterion, one of steps 168 and 204 determines whether the event represented by the new peak falls within the predetermined window. If not, the program backtracks by determining not to produce a new event signal and to open the window (one of steps 230 and 232, depending on the present mode of operation). The system also performs a "warm restart" (one of steps 234 and 236, depending on mode of operation), i.e. the alternate flag is reset and Last Peak is set to zero. However, the data in both the template register and the data register is unaffected by a warm restart. In addition, when in the low heart rate mode, the program thereupon switches to the high heart rate mode, as a part of the restart procedure. See step 238 in FIG. 4C.

It will be appreciated that the present invention is useful not only with nondirectional Doppler systems, but also with directional Doppler systems. Furthermore, it is useful both in continuous wave Doppler systems and in pulsed Doppler systems. For example, the circuitry of FIG. 1 can be modified to operate as a pulsed Doppler system. If so, range gating techniques may be employed to accept return signals only within the range of the fetal heart, thus to eliminate near field (skin) noise and acoustic crosstalk from the transmit to the receive transducer. Also, time gain compensation (TGC) techniques may be utilized to advantage to compensate for signal attenuation which increases with the range of the received echo signals.

The terms and expressions which have been employed are used as terms of description and not of limitation, and there is no intention in the use of such terms and expressions of excluding any equivalents of the features shown and described, or portions thereof, it being recognized that various modifications are possible within the scope of the invention claimed.

I claim:

1. A method of producing an event signal representative of the recurrence of a fetal heart cycle event comprising the steps of:
   supplying an input signal representative of fetal heart motions and corresponding to at least one fetal heart cycle;
   sampling portions of the input signal;
   deriving a comparison signal from the sampled portions of the input signal;
   providing a correlation signal which has peaks and which represents a correlation function in time between sampled portions of the input signal and the comparison signal;
   determining whether a fetal heart cycle is represented by one or two successive peaks of the correlation signal; and
   producing said event signal in response to said determination.

2. A method as in claim 1; wherein said determination comprises examining the amplitudes of said two successive peaks of the correlation signal.

3. A method as in claim 2; wherein the method further comprises updating the comparison signal by substituting for the comparison signal sampled portions of the input signal sampled prior to said determination.

4. A method as in claim 3; wherein said updating occurs following the occurrence of the latter in time of said two successive peaks.

5. A method as in claim 2; wherein said examination comprises identifying whether the amplitude of the latter in time of said two successive peaks exceeds the amplitude of the former in time of said two successive peaks by a predetermined value.

6. A method as in claim 5; wherein said determination further comprises checking the time duration between successive event signals against a predetermined time period.

7. A system for producing an event signal representative of the recurrence of a fetal heart cycle event comprising:
   supply means for supplying a data signal which represents fetal heart motions and which corresponds to at least one fetal heart cycle;
   sampling means for sampling portions of the data signal;
   deriving means for deriving a comparison signal from the sampled portions of the data signal; and
   data processing means for producing a correlation signal representative of a correlation function in time between the sampled portions of the data signal and the comparison signal; wherein the data processing means comprises determining means operable for determining whether a fetal heart cycle is represented by one or two successive peaks of the correlation signal; and event means for producing said event signal in response to said determination.

8. A system as in claim 7; wherein the determining means comprises examining means for examining the amplitudes of said two successive peaks of the correlation signal and for identifying whether the amplitude of the latter in time of said two successive peaks exceeds the amplitude of the former in time of said two successive peaks by a predetermined amount.

9. The system as in claim 8; wherein the determining means further comprises checking means for checking the time duration between event signals against a predetermined time period.

10. The system as in claim 9; wherein the data processing means further comprises updating means for updating the comparison signal by substituting for the comparison signal sampled portions of the data signal sampled prior to operation of said determining means.

11. The system as in claim 10; wherein the data processing means comprises a digital central processing means having an N bit data bus and a digital multipler-/accumulator unit; the multiplier/accumulator unit operative to provide the correlation signal by summing digitized values of the sampled data signal multiplied by respective digitized values of the comparison signal shifted in time relative to the sampled data signals, said correlation signal having a digital word length greater than N bits.

12. The system as in claim 11; wherein the data processing means further comprises AGC means for selecting the most significant, non-zero bits of the correlation signal.

13. The system as in claim 12; wherein said selection by the AGC means occurs prior to operation of said determining means.

* * * * *